United States Patent
Wang et al.

(10) Patent No.: US 6,355,081 B1
(45) Date of Patent: Mar. 12, 2002

(54) OLEOPHOBIC FILTER MATERIALS FOR FILTER VENTING APPLICATIONS

(75) Inventors: I-fan Wang; Richard McDonogh, both of San Diego, CA (US)

(73) Assignee: USF Filtration and Separations Group, Inc., Timonium, MD (US)

( * ) Notice: Subject to any disclaimer, the term of this patent is extended or adjusted under 35 U.S.C. 154(b) by 0 days.

(21) Appl. No.: 09/323,709

(22) Filed: Jun. 1, 1999

(51) Int. Cl.[7] ............................. B01D 71/06; B32B 9/04
(52) U.S. Cl. ...................... 55/524; 55/DIG. 5; 428/391; 428/447; 442/80
(58) Field of Search .............................. 55/524, DIG. 5; 96/11, 12; 428/378, 391, 447; 264/494, DIG. 48; 442/80, 81

(56) References Cited

U.S. PATENT DOCUMENTS

| | | | |
|---|---|---|---|
| 3,859,320 A | * | 1/1975 | Atherton |
| 3,870,767 A | | 3/1975 | Grimaud et al. |
| 4,032,502 A | * | 6/1977 | Lee et al. |
| 4,151,225 A | | 4/1979 | Buning |
| 4,270,933 A | * | 6/1981 | Meny et al. |
| 4,366,299 A | | 12/1982 | Dessaint |
| 4,483,901 A | * | 11/1984 | Okita et al. |
| 4,613,544 A | | 9/1986 | Burleigh |
| 4,764,560 A | | 8/1988 | Mitchell |
| 4,833,188 A | | 5/1989 | Kortmann et al. |
| 4,909,989 A | * | 3/1990 | Fukazawa et al. |
| 5,004,643 A | * | 4/1991 | Caldwell |
| 5,032,450 A | | 7/1991 | Rechlicz et al. |
| 5,066,683 A | | 11/1991 | Dillon et al. |
| 5,116,650 A | | 5/1992 | Bowser |
| 5,156,780 A | | 10/1992 | Kenigsberg et al. |
| 5,157,058 A | * | 10/1992 | Dillon et al. |
| 5,217,802 A | | 6/1993 | Scarmoutzos |
| 5,232,600 A | | 8/1993 | Degen et al. |
| 5,260,360 A | | 11/1993 | Mrozinski et al. |
| 5,286,279 A | | 2/1994 | Wu |
| 5,286,382 A | | 2/1994 | Scarmoutzos et al. |
| 5,352,513 A | | 10/1994 | Mrozinski et al. |
| 5,462,586 A | | 10/1995 | Sugiyama et al. |
| 5,554,414 A | | 9/1996 | Moya et al. |
| 5,706,804 A | * | 1/1998 | Baumann et al. |
| 5,856,246 A | | 1/1999 | Witzko et al. |
| 5,981,614 A | * | 11/1999 | Adiletta |
| 5,989,698 A | * | 11/1999 | Mrozinski et al. |
| 6,037,279 A | * | 3/2000 | Brookman et al. |
| 6,074,738 A | * | 6/2000 | Von Fragstein et al. |

FOREIGN PATENT DOCUMENTS

| | | |
|---|---|---|
| EP | 0 307 259 A1 | 3/1989 |
| EP | 0 615 799 A1 | 9/1994 |

* cited by examiner

*Primary Examiner*—David Simmons
*Assistant Examiner*—Fred Prince
(74) *Attorney, Agent, or Firm*—Knobbe, Martens, Olson & Bear LLP

(57) ABSTRACT

Oleophobic and hydrophobic filters for filter venting applications are made by forming a polydimethylsiloxane coating on the surface of a filtration substrate. The filters have high water penetration pressures and high air permeabilities. The coatings are formed by polymerizing vinyl terminated siloxane with a crosslinker such as hydrosilicone in the presence of a catalyst. Alternatively, the coatings can be formed by heat curing after exposing the substrate to methyl silicone and crosslinking at high temperature.

78 Claims, No Drawings

OLEOPHOBIC FILTER MATERIALS FOR FILTER VENTING APPLICATIONS

BACKGROUND OF THE INVENTION

1. Field of the Invention

The present invention relates to filters having both hydrophobic (water repellent) and oleophobic (oil repellent) properties. The properties are produced by forming a dimethylsiloxane coating on a substrate such as a hydrophobic or hydrophilic membrane or other filtration medium.

2. Background of the Invention

Hydrophobic filters are used in filtration of gases, in venting filters, and as gas vents. These hydrophobic filters allow gases and vapors to pass through the filter while liquid water is repelled by the filter.

Polytetrafluoroethylene (PTFE) has been the most common material in filters for gas venting. PTFE is chemically and biologically inert, has high stability, and is hydrophobic. PTFE filters therefore allow gases to be selectively vented while being impervious to liquid water.

Hydrophobic membranes are used as filters in healthcare and related industries, for example, as vent filters for intravenous (IV) fluids and other medical devices. In the health industry, the membrane must be sterilized before use. PTFE membranes can be sterilized for these health-related applications with steam or by chemical sterilization without losing integrity.

Treating PTFE membranes with steam can cause pore blockage due to condensation of oil from the machinery used to generate the steam. The resulting loss of air permeability reduces the membrane's ability to serve as an air vent. Although chemical sterilization minimizes exposure of the membrane to oil, chemical sterilization uses toxic chemicals and can generate byproducts which cause waste disposal problems. Ionizing radiation has also been used for sterilization of materials used in medical and biological devices. PTFE is unstable toward ionizing radiation. Irradiated PTFE membranes have greatly reduced mechanical strength and cannot be used in applications where they are subjected to even moderate pressures.

Perhaps the two biggest drawbacks to PTFE as a filter for venting gases are the high cost and the low air permeability of PTFE membranes. PTFE membranes are formed by extruding and stretching PTFE. Both the PTFE raw material and the processing to form the PTFE membranes are expensive. Further, the extruding and stretching processes used to form PTFE membranes create a membrane which has relatively low air permeability.

The oleophobicity of PTFE can be improved by impregnating or coextruding the PTFE with siloxanes (for example, U.S. Pat. No. 4,764,560), fluorinated urethane (U.S. Pat. No. 5,286,279), or perfluoro-2,2-dimethyl-1,3-dioxole (U.S. Pat. No. 5,116,650). Although the oil resistance of the PTFE is improved, the treated PTFE membranes are expensive, and air permeability remains fairly low.

As a result, efforts have been made to identify alternative substrates which are less expensive and have higher air permeability than PTFE and which can be modified to be hydrophobic and oleophobic.

Coating filtration substrates allows one to retain the desirable bulk properties of the substrate while only altering the surface and interfacial properties of the substrate. Coating substrates to increase their hydrophobic and oleophobic properties has not been very practical, because the coatings can reduce permeability. Furthermore, many of the coating materials are expensive.

Scarmoutzos (U.S. Pat. No. 5,217,802) modified the surface of substrates made of nylon, polyvinylidene difluoride (PVDF), and cellulose by treating the substrate with a fluorinated acrylate monomer. The substrate was sandwiched between two sheets of polyethylene, and the monomer was polymerized by exposing to ultraviolet light. The resulting composite filters had hydrophobic and oleophobic surfaces. The air permeability of the filters decreases with time.

Moya (U.S. Pat. No. 5,554,414) formed composite filters from polyethersulfone and PVDF membranes with a method similar to that of Scarmoutzos. The resulting filters did not wet with water or hexane. The disadvantage of the Moya filters is that air permeability of the treated filters was lower than the untreated substrates, and the fluorinated monomer is expensive.

Sugiyama et al. (U.S. Pat. No. 5,462,5856) treated nylon fabric and PTFE membranes with solutions containing two different preformed fluoropolymers. The treated filters were resistant to water and oils. The durability of filters coated with preformed polymers is often less than that for filters where the coating is formed by polymerizing a monomer on the surface of the substrate.

Kenigsberg et al. (U.S. Pat. No. 5,156,780) treated a variety of membranes and fabrics with solutions of fluoroacrylate monomers and formed coatings on the substrate by polymerizing the monomer. The coating conferred oil and water repellency onto the substrate. However, the air flow through the treated membrane was reduced, compared to the untreated membrane.

Hydrophobic media suitable for garments have been made by extruding mixtures of polypropylene or PTFE and the fluorochemical oxazolidinone as disclosed in U.S. Pat. No. 5,260,360. The media made by extruding tend to have relatively low air permeability.

There is a need for an oleophobic and hydrophobic filter which is inexpensive and has high air permeability. Specifically, there is a need for a coating for filter medium substrates that makes the substrate oleophobic and hydrophobic, and for a more cost effective process of making oleophobic filters.

SUMMARY OF THE INVENTION

The present invention provides an oleophobic, hydrophobic, coated filter, including a substrate, the substrate having a pressure of water penetration, the coated filter further including a coating derived from a coating formulation, wherein the coating is permanently crosslinked to the substrate, and wherein the coating formulation includes a vinyl-terminated siloxane polymer, and wherein the coated filter has a pressure of water penetration at least 10 percent greater than the pressure of water penetration of the substrate without the coating. The substrate may include a porous polymeric membrane, a nonwoven material, or a woven material. The substrate may include a polymer such as polysulfone, polyethersulfone, polyarylsulfone, polyvinylidene fluoride, polypropylene, polyethylene, poly(tetrafluoroethylene), poly(tetrafluoroethylene-co-ethylene), nylon, or cellulosic esters. The siloxane polymer may include a vinyldimethyl-terminated siloxane. The coating formulation may further include a crosslinker, such as, for example, methylhydro,cyanopropylmethylsiloxane; methylhydro,phenylmethylsiloxane; methylhydro,methyloctylsiloxane; methyltriacetoxy silane; or methyl silicone. The coating formulation may further include a crosslinker catalyst. The filter of the invention may also be bonded to a fabric.

In another aspect of the invention, there is provided a method of producing a hydrophobic, oleophobic filter, including the steps of providing a substrate having a first pressure of water penetration; contacting the substrate with a coating formulation including a vinyl-terminated siloxane polymer to produce a coated filter; crosslinking the coating formulation to the filter; and recovering an oleophobic, hydrophobic, permanently coated filter having a second pressure of water penetration, wherein the second pressure of water penetration is at least 10 percent greater than the first pressure of water penetration. In this method, the substrate may include a porous polymeric membrane, a nonwoven material, or a woven material. The substrate may include a polymer such as polysulfone, polyethersulfone, polyarylsulfone, polyvinylidene fluoride, polypropylene, polyethylene, poly(tetrafluoroethylene), poly(tetrafluoroethylene-co-ethylene), nylon, or cellulosic esters. The siloxane polymer may include a vinyldimethyl-terminated siloxane. The coating formulation may further include a crosslinker, such as, for example, methylhydro, cyanopropylmethylsiloxane; methylhydro, phenylmethylsiloxane; methylhydro,methyl-octylsiloxane; methyltriacetoxy silane; or methyl silicone. The coating formulation may further include a crosslinker catalyst. The filter of the invention may also be bonded to a fabric. The crosslinking step may include exposing the coated filter to a temperature sufficient to facilitate a crosslinking activity of the crosslinker. The coating formulation further may include a crosslinker catalyst. The crosslinking step may also include exposing the coated filter to water or water vapor, or exposing the coated filter to ultraviolet radiation.

DETAILED DESCRIPTION OF THE PREFERRED EMBODIMENT

The present invention relates to hydrophobic and oleophobic filters that have high gas permeabilities and that repel water and other liquids. The invention also relates to methods of preparing such filters.

The filter medium substrate is treated with a coating material comprising crosslinked vinyldimethyl terminated siloxane, which treatment coats the surface of the substrate. Coating the substrate with a material comprising crosslinked vinyldimethyl terminated siloxane gives permanent oleophobicity and hydrophobicity to the filter. The treated filters have high permeabilities for air flow and reject liquid water, as evidenced by high water penetration pressures. The filters are useful, for example, as air filters or vent filters for intravenous (IV) or other medical devices. The critical surface tension for spreading ($y_c$), which is defined as the wettability of a solid surface by noting the lowest surface tension a liquid can have and still exhibit a contact angle ($\theta$) greater than zero degrees on that solid, was dramatically reduced after treatment of the substrates according to the process of the invention.

The process can be used to coat substrates made from sulfone polymers such as polysulfone, polyethersuflone, or polyarylsulfone, as well as other polymers, such as polyvinylidene fluoride (PVDF), polytetrafluoroethylene (PTFE), polyolefins including polyethylene and polypropylene, poly(tetrafluoroethylene-co-ethylene) (ECTFE), acrylic copolymers, polyamides, polyesters, and polyurethanes.

For the present invention, substrates may include not only flat sheet polymer membranes made from casting a polymer-solvent-nonsolvent dope mix, but substrates may also refer to any other suitable filtration or exclusion medium. Non-limiting examples of other media within the meaning of substrate include hollow fibers, melt blown or other nonwoven media, woven media, or sedimented structures. In addition, filters of the present invention may be composites, such as, for example, composites having different layers of any of the foregoing media, composites having multiple layers of the same medium, or composites having layers of the same medium, but of different pore sizes, porosities, geometries, orientations, and the like.

In accordance with the invention, the substrate can be coated by any workable method. A few examples of approaches to coat formation are provided herein.

However, the possible useful coating methods are not limited to the methods listed below:

1. Crosslinking the coat formulation to the substrate by moisture curing polydimethyl siloxane with the crosslinker methyltriacetoxy silane.
2. Polymerizing vinyl terminated siloxane (structure I, below) with a crosslinker such as hydrosilicone in the presence of a catalyst. The reaction is shown below.
3. Crosslinking a coating to a substrate by curing a siloxane coating on a substrate by exposure to ultraviolet (UV) radiation.
4. Heat crosslinking with methyl silicone at a temperature above 100° C.

In the first method, the substrate is impregnated with polydimethyl siloxane and the crosslinker methyltriacetoxy silane to form a coat on the substrate. The coat is then cured with moisture to further bond the coat to the substrate. The moisture in the air slowly cures the siloxane polymers in a process that may require more than 12 hours. The moisture cure systems can employ the most common crosslinkers such as, for example, acyloxy, enoxy, and oxime crosslinkers.

In the second method of forming the coating, a vinyl terminated siloxane is reacted with a crosslinker such as hydrosilicone in the presence of a catalyst. The structure of the vinyl terminated siloxane is shown below as I:

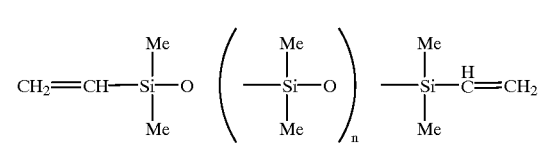

The reaction which occurs between the vinyl terminated siloxane and the hydrosilicone is:

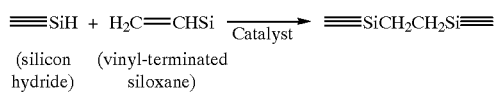

The vinyl terminated siloxane can have one or more vinyl groups. The weight % of vinyl groups can range from 0.1 to 0.4 wt %. The viscosity of the vinyl terminated siloxane can be from 500 to 70,000 centipoise (cps), more preferably from 800 to 10,000 cps, and most preferably from 1,000 to 5,000 cps The crosslinker is a compound which contains one or more silicon-hydrogen bonds. Hydrosilicone is an exemplary crosslinker. Methylhydro, trimethylsilyl-terminated dimethylsiloxane is another preferred crosslinker. In a preferred embodiment, the crosslinker, hydrosilicone, has viscosity of 25–35 cps and a molecular weight of 500 to 10,000 Daltons. The weight % of the methylhydro units in the polymer is about 15 to 50%. Other crosslinkers, such as methylhydro,cyanopropylmethylsiloxane, methylhydro, methyloctyl siloxane, and dimethylsiloxy-terminated methylhydro,phenylmethyl siloxane also can be used. The silicon-hydrogen bond of the crosslinker reacts with the double bond of the vinyl group of the vinyl terminated siloxane. The weight ratio of vinyl terminated siloxane to crosslinker is between 20 and 0.1, more preferably between 15 and 0.5, and most preferably between 10 and 1.

In many crosslinker/catalyst formulations, the formulation may contain 5–10 ppm platinum, which is preferably in the form of platinum 1,3-diethylenyl-1,1,3,3-tetramethyldisiloxane complexes. Platinum divinyltetramethylsiloxane complex is an exemplary noble metal catalyst for forming the coating of the invention. The noble metal catalyst is normally present in a concentration of 1 to 100 ppm, more preferably 5 to 10 ppm, calculated as the weight of the noble metal catalyst. The noble metal catalyst can be formed in-situ, or it can be formed prior to addition to a reaction solution. Although the noble metal catalyst can be insoluble or soluble in the reaction solution, it is generally preferred that the noble metal catalyst be soluble in the reaction solution. Nonlimiting examples of noble metals are nickel, copper, palladium, silver, platinum, and gold. Other catalysts such as zinc and tin chlorides, zinc acetates, zinc octoates, and peroxides can also be used.

The vinyl terminated siloxane, crosslinker, and noble metal catalyst may be dissolved in a solvent. The solvent may be a hydrocarbon such as, for example, hexane or toluene. The selected solvent should not react with or dissolve the substrate or the crosslinked coating.

The coating formulation containing the vinyl terminated siloxane, crosslinker, noble metal catalyst, and solvent, is contacted with the substrate at a temperature between 15 and 30° C. In a preferred embodiment, the contacting takes place at approximately room temperature. The two part crosslinker systems thus may include catalysts and silanol-terminated polymers with a molecular weight of about 26,000 to 200,000 Daltons.

The substrate is soaked in the solution for about 15 seconds to 5 minutes, more preferably 30 seconds to 3 minutes, and most preferably 1 to 2 minutes. The coated substrate is then removed from the coating solution and is air dried for 1 to 180 minutes, then oven cured at a temperature of 100 to 150° C., more preferably 105 to 130° C., and most preferably 110 to 120° C. for 1 to 180 minutes, more preferably 5 to 120 minutes, and most preferably 10 to 60 minutes, to produce the coated filter of the invention.

As a third alternative, crosslinking may be achieved by impregnating the substrate with polydimethyl siloxane and then exposed to ultraviolet (UV) radiation to cure the coating on the substrate. Likewise, in a fourth embodiment, methyl silicone may be impregnated into the substrate to form the coat, and the coat then may be crosslinked by heat curing at a temperature above 100° C.

Vinyl-terminated siloxanes or vinyl-terminated fluorosiloxanes may be dissolved in a solvent selected from the group consisting of fluorocarbons, hydrocarbons, and alcohols such as, for example, isopropanol. Preferably, the solvent is not a solvent of the substrate, and can be a hydrocarbon such as, for example, hexane. The solution containing solvent and vinyl-terminated siloxanes and crosslinkers is contacted with the substrate at a temperature of about 15 to 30° C. for about 30 seconds to 5 minutes. Preferably, the contacting takes place at approximately room temperature for several seconds to 2 minutes.

Embodiments of the coating process can be used to coat substrates including asymmetric or isotropic membranes, or other media such as, for example, melt blown, woven, and non woven material. Melt blown material may include polypropylene or ECTFE, and are commercially available from U.S. Filter/Filtrate Division, Timonium, MD.

The substrate can be treated with sufficient coating agent so that the coated filter contains at least 0.1 wt % of the coat comprising vinyldimethyl-terminated siloxane, more preferably between 0.5 and 6 wt % coat material, and most preferably 1 to 3 wt % coat material.

The hydrophobic, oleophobic filters of the invention, employing any useful substrate, also can be bonded to a textile fabric or other woven or nonwoven material to form a layered fabric capable of excluding the passage of liquid while allowing passage of vapors and gasses therethrough. Such a layered fabric can be useful in a variety of applications, as will be appreciated by those or ordinary skill in the art. Bonding a hydrophobic, oleophobic filter to a fabric can be accomplished by conventional adhesives, thermal bonding, and the like, and can also be achieved by layering the filtration medium substrate together with the fabric, and curing or otherwise crosslinking the coating formulation thereafter. In this embodiment, the substrate may be coated prior to layering, or the coating may be simultaneously with, or after, the layering of substrate with fabric.

EXAMPLES

The following examples are provided to illustrate the present invention. However, such examples are merely illustrative and are not intended to limit the subject matter of the application.

The first three examples demonstrate the modification of the surfaces of substrates having three different pore sizes by chemical crosslinking.

Example 1

Oleophobic Modification of Very Large Pore Microfiltration Membranes by Chemical Crosslinking A 1.8 µm polysulfone membrane (BTS-X, sold by US Filter, San Diego, Calif.) was treated with a hexane solution containing 1% by weight vinyldimethyl terminated siloxane (available from United Chemical Technologies (UCT), Bristol, Pa.), 0.1 wt % hydrosilicone (also available from UCT), and 10 ppm platinum divinyltetramethyldisiloxane catalyst ( also available from UCT). The membrane was soaked for a few seconds in the solution. The membrane was then air dried for one minute and oven cured at 140° C. for 10 minutes (Example 1a) or 15 minutes (Example 1b).

The weight percent of coating on the filter was determined in all of the examples by weighing the filters before and after treatment. The weight gain divided by the total weight of the filter after treatment is the weight percent. A filter weighing 99 mg before treatment and 100 mg after treatment would have a coating value of 1 wt %. The average coating value for filters treated according to Example 1 is about 1 wt %.

The resulting samples were tested for water penetration pressure and air flow. Both tests were performed with a 90 mm disk, having an effective filtration area of about 45 cm$^2$. The results are shown in Table 1. The water penetration pressures of the treated filters were 20% (Example 1a) and 40% (Example 1b) higher than for the untreated substrate. The air flow rates for the treated filters were equal (Example 1a) and 10% higher (Example 1b) than for the untreated substrate.

Example 2

Oleophobic Modification of Large Pore Microfiltration Membranes by Chemical Crosslinking A 1.2 μm polysulfone membrane (BTS-5H, US Filter, San Diego, Calif.) was treated with a hexane solution containing (Example 2a) 1% by weight vinyldimethyl terminated siloxane, 0.1 wt % hydrosilicone, and 10 ppm platinum divinyltetramethyldisiloxane catalyst or (Example 2b) 2% by weight vinyldimethyl terminated siloxane, 0.2 wt % hydrosilicone, and 20 ppm platinum divinyltetramethyldisiloxane. Each membrane was soaked for a few seconds in the solution. The membranes were air dried for one minute then oven cured at 140° C. for 30 minutes.

The resulting samples were tested for water penetration pressure and air flow. Both tests were performed with a 90 mm disk. The results are shown in Table 1. The water penetration pressures of the treated membranes were 57% (Example 2a) and 43% (Example 2b) higher than the untreated membrane. The air flow rates for the treated membranes were 80% (Example 2a) and 8% (Example 2b) higher than for the untreated membrane.

The substrate of Example 2a was reacted with twice as much siloxane, silane, and catalyst as the substrate of Example 2b. The air flow of the filter of Example 2a was higher than the air flow for the filter of Example 2b. The higher concentration of components in the coating compound in the filter of Example 2b led to a relatively lower air flow.

Example 3

Oleophobic Modification of a Smaller Pore Microfiltration Membrane by Chemical Crosslinking A 0.2 μm hydrophobic polysulfone membrane (BTS-55H, US Filter, San Diego, Calif.) was treated with a hexane solution containing 1% by weight vinyldimethyl terminated siloxane, 0.1 wt % hydrosilicone, and 10 ppm platinum divinyltetramethyldisiloxane catalyst. The substrate was soaked in the solution for a few seconds. The filter was air dried for one minute, then oven cured at 140° C. for 15 minutes.

The resulting filter was tested for water penetration pressure and air flow. Both tests were performed with a 90 mm disk. The results are shown in Table 1. The water penetration pressure of the treated filter was 62% higher than for the untreated substrate. The air flow rate for the treated filter was 13% lower than for the untreated substrate.

The following example shows that the treatment can be effectively performed using either hydrophobic or hydrophilic substrates.

Example 4

Oleophobic Modification of Hydrophobic and Hydrophilic Microfiltration Membranes by Chemical Crosslinking Hydrophobic (Example 4a) and hydrophilic (Example 4b) 0.45 μm polysulfone membranes (BTS-25H and BTS-25, US Filter, San Diego, Calif.) were treated with a hexane solution containing 1% by weight vinyldimethyl terminated siloxane, 0.1 wt % hydrosilicone, and 10 ppm platinum divinyltetramethyldisiloxane catalyst. The membranes were soaked in the solution for a few seconds, air dried for one minute, then oven cured at 140° C. for 15 minutes.

The resulting samples were tested for water penetration pressure and air flow. Both tests were performed with a 90 mm disk. The results are shown in Table 1. The water penetration pressure of the treated filter was 9% higher (Example 4a) than for the untreated substrate. The hydrophilic membrane of Example 4b had a water penetration pressure of 0 psi before treatment and 30 psi after treatment. The air flow rates for the treated filters were both about 20% lower than for the corresponding untreated substrates.

TABLE 1

Air Flow and Water Penetration Results for Untreated Substrates Compared with Filters Treated by Chemical Crosslinking

| Example Number | Air Flow* | Air Flow Change† | Water Penetration Pressure* | Water Penetration Pressure Change† |
|---|---|---|---|---|
| 1 (Control) | 55.7 | — | 5 | — |
| 1a | 55.7 | none | 6 | +20% |
| 1b | 61.2 | +10% | 7 | +40% |
| 2 (Control) | 18.9 | — | 7 | — |
| 2a | 34 | +80% | 11 | +57% |
| 2b | 20.4 | +8% | 10 | +43% |
| 3 (Control) | 9.2 | — | 26 | — |
| 3 | 8 | −13% | 42 | +62% |
| 4a (Control) | 13.6 | — | 20 | — |
| 4a | 10.9 | −20% | 38 | +90% |
| 4b (Control) | 13.6 | — | 0 | — |
| 4b | 10.9 | −20% | 30 | undefined (∞) |

*Air flow is expressed in units of (ml/min/cm-$H_2O$/cm$^2$). Water penetration pressure is expressed in psi.
†Changes in air flow and water penetration are compared to control values for each example.

The examples in Table 1 show that substrates having a wide range of pore sizes can be made oleophobic and hydrophobic by being coated with a coat comprising polydimethylsiloxane. Further, both hydrophobic and hydrophilic substrates can be treated to be hydrophobic and oleophobic.

In the following example, the coat was made by heat crosslinking rather than by chemical crosslinking.

Example 5

Oleophobic Modification of Large Pore Microfiltration Membranes by Heat Crosslinking A solution containing 50 wt % methyltrimethoxysilane (available from UCT) and 50 wt % isopropylalcohol (IPA) was prepared. Two moles of water per mole of methyltrimethoxysilane were added to the methyltrimethoxysilane/IPA solution. The combined solution was then heated at 60–70° C. for several hours to hydrolyze the methyltrimethoxysilane. The resulting solution was then diluted with IPA to 2 wt % of the polymer.

The solution was used to coat a large pore hydrophobic polysulfone microfiltration membrane with a pore size of 1.2 μm (BTS-5H). The substrate was soaked for a few seconds, air dried for one minute, then heat crosslinked at 140° C. for 12 minutes. A 90 mm disk of the crosslinked filter was tested for water penetration pressure and air flow. The results are shown in Table 2. The coated filter had a higher water penetration pressure than the untreated substrate (15 psi versus 7 psi). The air flow rate for the treated filter was 20% higher than the air flow rate for the untreated substrate.

TABLE 2

Air Flow and Water Penetration Results for an Untreated Substrate Compared with a Filter Treated by Heat Crosslinking

| Example Number | Air Flow* | Air Flow Change† | Water Penetration Pressure* | Water Penetration Pressure Change† |
|---|---|---|---|---|
| 5 (Control) | 18.9 | — | 7 | — |
| 5 | 22.7 | +20% | 15 | +114% |

*Air flow is expressed in units of (ml/min/cm-$H_2O$/cm$^2$). Water penetration pressure is expressed in psi.
†Changes in air flow rate and water penetration are compared to control values for each example.

In the following example, a polyvinylidene difluoride membrane was treated by chemical crosslinking, demonstrating that a variety of substrates can be treated according to the invention.

Example 6

Oleophobic Modification of a Hydrophilic PVDF Microfiltration Membrane by Chemical Crosslinking A 1.0 μm hydrophilic polyvinylidene difluoride (PVDF) membrane (commercially available from U.S. Filter/Filtration Division, San Diego, Calif.) was treated with a hexane solution containing 1% by weight vinyldimethyl terminated siloxane, 0.1 wt % hydrosilicone, and 10 ppm platinum divinyltetramethyldisiloxane catalyst. The substrate was soaked for a few seconds in the solution. The membrane was air dried for one minute then oven cured at 140° C. for 15 minutes.

The resulting filter was tested for water penetration pressure and air flow. Both tests were performed with a 90 mm disk. The results are shown in Table 3. The water penetration pressure of the treated filter was 5 psi versus 0 psi for the untreated substrate. The hydrophobicity of the treated filter was therefore increased by the treatment. The air flow rate for the treated filter was 28% lower than the air flow rate for the untreated substrate.

TABLE 3

Air Flow and Water Penetration Results for an Untreated PVDF Membrane Compared with a PVDF Membrane Treated by Chemical Crosslinking

| Example Number | Air Flow* | Air Flow Change† | Water Penetration Pressure* | Water Penetration Pressure Change† |
|---|---|---|---|---|
| 6 (Control) | 29.2 | — | 0 | — |
| 6 | 21.1 | −28% | 5 | undefined (∞) |

*Air flow is expressed in units of (ml/min/cm-$H_2O$/cm$^2$). Water penetration pressure is expressed in psi.
†Changes in air flow rate and water penetration are compared to control values for each example.

Treating the PVDF membrane to form a coat comprising polydimethylsiloxane therefore made the hydrophilic PVDF hydrophobic.

Example 7

Laminated Oleophobic Filters

Filters from Example 2 were laminated to a nonwoven polyester substrate, Hollytex 3256, with a layer of polyethylene (PE85) in between the filter and the polyester substrate. Hollytex 3256 is commercially available from Ahlstrom, Mount Holly Spring, Pa.; PE85 is commercially available from Bostic, Inc., Dana Point, Calif. Lamination setup temperature was about 138° C. The resulting laminated oleophobic filters displayed improved mechanical strength as compared with the filter or the polyester substrate alone, and were also tested for air flow rate and water penetration pressure. The air flow was the same as in Example 2b, and the water penetration pressure was further improved to be about 17 psi as compared to 10 psi from Example 2b.

Example 8

Determination of Oleophobic Nature of Modified Filters

The relative oleophobicity of modified filters and unmodified substrates is determined by testing the filters and substrates (collectively, filtration media) for their ability to be wetted by a low surface-tension fluid. A drop of 2-methoxyethanol is gently placed on the surface of the filtration medium using a glass pipette, and the wetting time is recorded. If the medium is not wetted by the 2-methoxyethanol within 30 seconds, the result is recorded as "No Wetting". Filters of the invention are generally resistant to wetting by 2-methoxyethanol, and are relatively more oleophobic than untreated substrates.

EQUIVALENTS

The present invention has been described in connection with specific embodiments thereof. It will be understood that it is capable of further modification, and this application is intended to cover any variations, uses, or adaptations of the invention following, in general, the principles of the invention and including such departures from the present disclosure as come within known or customary practices in the art to which the invention pertains and as may be applied to the essential features hereinbefore set forth, and as fall within the scope of the invention and any equivalents thereof.

What is claimed is:

1. A vent filter for a medical device, the vent filter comprising an oleophobic, hydrophobic, coated substrate, the substrate having a pressure of water penetration and an air permeability, the coated filter further comprising a coating derived from a coating formulation, wherein the coating is permanently crosslinked to the substrate, and wherein the coating formulation comprises a vinyl-terminated siloxane polymer, wherein the vent filter may be steam sterilized or chemically sterilized without substantial loss of air permeability.

2. The coated filter of claim 1, wherein the substrate comprises a porous polymeric membrane, a nonwoven material, or a woven material.

3. The coated filter of claim 2, wherein the porous polymeric membrane comprises an asymmetric membrane.

4. The coated filter of claim 2, wherein the porous polymeric membrane comprises an isotropic membrane.

5. The coated filter of claim 1, wherein the substrate comprises a polymer selected from the group consisting of polysulfone, polyethersulfone, polyarylsulfone, polyvinylidene fluoride, poly(tetrafluoroethylene), poly (tetrafluoroethylene-co-ethylene), nylon, polyolefin, polyester, acrylic copolymer, polyamide, polyurethane, and cellulosic esters.

6. The coated filter of claim 5, wherein the polyolefin comprises polypropylene or polyethylene.

7. The coated filter of claim 1, wherein the siloxane polymer comprises a vinyldimethyl-terminated siloxane.

8. The coated filter of claim 1, wherein the coating formulation further comprises a crosslinker.

9. The coated filter of claim 8, wherein the crosslinker is selected from the group consisting of: methylhydro, cyanopropylmethylsiloxane; methylhydro, phenylmethylsiloxane; methylhydro,methyl-octylsiloxane; methyltriacetoxy silane; and methyl silicone.

10. The coated filter of claim 8, wherein the coating formulation further comprises a crosslinker catalyst.

11. The coated filter of claim 1, bonded to a fabric.

12. The coated filter of claim 1, wherein the coated filter has a pressure of water penetration at least 10 percent greater than the pressure of water penetration of the substrate without said coating.

13. The coated filter of claim 1, wherein the vinyl-terminated siloxane polymer comprises a vinyl-terminated fluorosiloxane polymer.

14. A laminate comprising the coated filter of claim 1.

15. A method of producing a vent filter for a medical device comprising a hydrophobic, oleophobic filter, comprising the steps of:
   providing a substrate having a first pressure of water penetration;
   contacting the substrate with a coating formulation comprising a vinyl-terminated siloxane polymer to produce a coated filter;
   crosslinking the coating formulation to the filter;
   recovering an oleophobic, hydrophobic, permanently coated filter having a second pressure of water penetration and an air permeability; and
   incorporating the oleophobic, hydrophobic permanently coated filter into a vent filter for a medical device, wherein the vent filter may be steam sterilized or chemically sterilized without substantial loss of air permeability.

16. The method of claim 15, wherein the substrate comprises a porous polymeric membrane, a nonwoven material, or a woven material.

17. The method of claim 15, wherein the substrate comprises a polymer selected from the group consisting of polysulfone, polyethersulfone, polyarylsulfone, polyvinylidene fluoride, poly(tetrafluoroethylene), poly (tetrafluoroethylene-co-ethylene), nylon, polylefin, polyester, acrylic copolymer, polyamide, polyurethane, and cellulosic esters.

18. The method of claim 17, wherein the polyolefin comprises polypropylene or polyethylene.

19. The method of claim 15, wherein the siloxane polymer comprises a vinyldimethyl-terminated siloxane.

20. The method of claim 15, wherein the coating formulation further comprises a crosslinker.

21. The method of claim 20, wherein the crosslinker is selected from the group consisting of: methylhydro, cyanopropylmethylsiloxane; methylhydro, phenylmethylsiloxane; methylhydro,methyl-octylsiloxane; methyltriacetoxy silane; and methyl silicone.

22. The method of claim 20, wherein the crosslinking step comprises exposing the coated filter to a temperature sufficient to facilitate a crosslinking activity of the crosslinker.

23. The method of claim 20, wherein the coating formulation further comprises a crosslinker catalyst.

24. The method of claim 15, wherein the crosslinking step comprises exposing the coated filter to water or water vapor.

25. The method of claim 15, wherein the crosslinking step comprises exposing the coated filter to ultraviolet radiation.

26. The method of claim 15, wherein the second pressure of water penetration is at least 10 percent greater than the first pressure of water penetration.

27. The method of claim 15, wherein the vinyl-terminated siloxane polymer comprises a vinyl-terminated fluorosiloxane polymer.

28. A vent filter for a medical device, the vent filter comprising an oleophobic, hydrophobic, coated substrate having a pressure of water penetration and an air permeability, the coated filter further comprising a coating derived from a coating formulation, wherein the coating is permanently crosslinked to the substrate and comprises a polysiloxane, and wherein the substrate comprises a polymer selected from the group consisting of polysulfone, polyethersulfone, and polyarylsulfone, wherein the vent filter may be steam sterilized or chemically sterilized without substantial loss of air permeability.

29. The coated filter of claim 28, wherein the substrate comprises a porous polymeric membrane.

30. The coated filter of claim 29, wherein the porous polymeric membrane comprises an asymmetric membrane.

31. The coated filter of claim 29, wherein the porous polymeric membrane comprises an isotropic membrane.

32. The coated filter of claim 28, wherein the substrate comprises a nonwoven material or a woven material.

33. The coated filter of claim 28, wherein the coating formulation comprises a vinyl-terminated siloxane polymer.

34. The coated filter of claim 33, wherein the vinyl-terminated siloxane polymer comprises a vinyl-terminated fluorosiloxane polymer.

35. A laminate comprising the coated filter of claim 28.

36. The coated filter of claim 28, wherein the coated filter has a pressure of water penetration at least 10 percent greater than the pressure of water penetration of the substrate without said coating.

37. The coated filter of claim 28, wherein the coating formulation comprises methyl trimethoxysilane.

38. A vent filter for a medical device, the vent filter comprising an oleophobic, hydrophobic, coated substrate having a pressure of water penetration and an air permeability, the coated filter further comprising a coating dervied from a coating formulation, wherein the coating is permanently crosslinked to the substrate and comprises a polysiloxane, and wherein the substrate comprises a polymer selected from the group consisting of poly (tetrafluoroethylene-co-ethylene), nylon, polyolefin, polyester, acrylic copolymer, polyamide, polyurethane, and cellulosic esters, wherein the vent filter may be steam sterilized or chemically sterilized without substantial loss of air permeability.

39. The coated filter of claim 38, wherein the substrate comprises a porous polymeric membrane.

40. The coated filter of claim 39, wherein the porous polymeric membrane comprises an asymmetric membrane.

41. The coated filter of claim 39, wherein the porous polymeric membrane comprises an isotropic membrane.

42. The coated filter of claim 38, wherein the substrate comprises a nonwoven material or a woven material.

43. The coated filter of claim 38, wherein the coating formulation comprises a vinyl-terminated siloxane polymer.

44. The coated filter of claim 43, wherein the vinyl-terminated siloxane polymer comprises a vinyl-terminated fluorosiloxane polymer.

45. A laminate comprising the coated filter of claim 38.

46. The coated filter of claim 38, wherein the coated filter has a pressure of water penetration at least 10 percent greater than the pressure of water penetration of the substrate without said coating.

47. The coated filter of claim 38, wherein the coating formulation comprises methyl trimethoxysilane.

48. A vent filter for a medical device, the vent filter comprising an oleophobic, hydrophobic, coated filter comprising a substrate, the coated filter further comprising a coating derived from a coating formulation, wherein the coating is permanently crosslinked to the substrate, and wherein the coating formulation comprises methyl trimethoxysilane, the oleophobic, hydrophobic, coated filter having an air permeability, wherein the vent filter may be steam sterilized or chemically sterilized without substantial loss of air permeability.

49. The coated filter of claim 48, wherein the substrate comprises a polymer.

50. The coated filter of claim 49, wherein the polymer is selected from the group consisting of polysulfone, polyethersulfone, polyarylsulfone, polytetrafluoroethylene, poly(tetrafluoroethylene-co-ethylene), nylon, polyolefin, acrylic copolymer, polyamide, polyurethane, and cellulosic esters.

51. The coated filter of claim 48, wherein the substrate comprises a porous polymeric membrane.

52. The coated filter of claim 51, wherein the porous polymeric membrane comprises an asymmetric membrane.

53. The coated filter of claim 51, wherein the porous polymeric membrane comprises an isotropic membrane.

54. The coated filter of claim 51, wherein the coated filter has a pressure of water penetration at least 10 percent greater than the pressure of water penetration of the substrate without said coating.

55. A method of producing a vent filter for a medical device comprising a hydrophobic, oleophobic filter, comprising the steps of:
    providing a substrate having a first pressure of water penetration, wherein the substrate comprises a polymer selected from the group consisting of polysulfone, polyethersulfone, and polyarylsulfone;
    contacting the substrate with a coating formulation comprising a siloxane to produce a coated filter;
    crosslinking the coating formulation to the filter;
    recovering an oleophobic, hydrophobic, permanently coated filter having a second pressure of water penetration and an air permeability; and
    incorporating the oleophobic, hydrophobic, permanently coated filter into a vent filter for a medical device, wherein the vent filter may be steam sterilized or chemically sterilized without substantial loss of air permeability.

56. The method of claim 55, wherein the substrate comprises a porous polymeric membrane.

57. The method of claim 56, wherein the porous polymeric membrane comprises an asymmetric membrane.

58. The method of claim 56, wherein the porous polymeric membrane comprises an isotropic membrane.

59. The method of claim 55, wherein the coating formulation comprises methyl trimethoxysilane.

60. The method of claim 55, wherein the coating formulation comprises a vinyl-terminated siloxane polymer.

61. The method of claim 60, wherein the vinyl-terminated siloxane polymer comprises a vinyl-terminated fluorosiloxane polymer.

62. The method of claim 55, wherein second pressure of water penetration is at least 10 percent greater than the first pressure of water penetration.

63. A method of producing a vent filter for a medical device comprising a hydrophobic, oleophobic filter, comprising the steps of:
    providing a substrate having a first pressure of water penetration, wherein the substrate comprises a polymer selected from the group consisting of poly (tetrafluoroethylene-co-ethylene), nylon, polyolefin, polyester, acrylic copolymer, polyamide, polyurethane, and celluosic esters;
    contacting the substrate with a coating formulation comprising a siloxane to produce a coated filter;
    crosslinking the coating formulation to the filter;
    recovering an oleophobic, hydrophobic, permanently coated filter having a second pressure of water penetration and an air permeability; and
    incorporating the oleophobic, hydrophobic, permanently coated filter into a vent filter for a medical device, wherein the vent filter may be steam sterilized or chemically sterilized without substantial loss of air permeability.

64. The method of claim 63, wherein the substrate comprises a porous polymeric membrane.

65. The method of claim 64, wherein the porous polymeric membrane comprises an asymmetric membrane.

66. The method of claim 64, wherein the porous polymeric membrane comprises an isotropic membrane.

67. The method of claim 63, wherein the coating formulation comprises methyl trimethoxysilane.

68. The method of claim 63, wherein the coating formulation comprises a vinyl-terminated siloxane polymer.

69. The method of claim 63, wherein the vinyl-terminated siloxane polymer comprises a vinyl-terminated fluorosiloxane polymer.

70. The method of claim 63, wherein second pressure of water penetration is at least 10 percent greater than the first pressure of water penetration.

71. A method of producing a vent filter for a medical device comprising a hydrophobic, oleophobic filter, comprising the steps of:
    providing a substrate having a first pressure of water penetration;
    contacting the substrate with a coating formulation comprising methyl trimethoxysilane to produce a coated filter;
    crosslinking the coating formulation to the filter;
    recovering an oleophobic, hydrophobic, permanently coated filter having a second pressure of water penetration and an air permeability; and
    incorporating the oleophobic, hydrophobic, permanently coated filter into a vent filter for a medical device, wherein the vent filter may be steam sterilized or chemically sterilized without substantial loss of air permeability.

72. The method of claim 71, wherein the substrate comprises a porous polymeric membrane.

73. The method of claim 72, wehrein the substrate comprises a polymer.

74. The method of claim 73, wherein the polymer is selected from the group consisting of polysulfone, polyethersulfone, polyarylsulfone, polytetrafluoroethylene, poly(tetrafluoroethylene-co-ethylene), nylon, polyolefin, polyester, acrylic copolymer, polyamide, polyurethane, and cellulosic esters.

75. The method of claim 73, wherein the substrate comprises a porous polymeric membrane.

76. The method of claim 75, wherein the porous polymeric membrane comprises an asymmetric membrane.

77. The method of claim 75, wherein the porous polymeric membrane comprises an isotropic membrane.

78. The method of claim 71, wherein second pressure of water penetration is at least 10 percent greater than the first pressure of water penetration.

* * * * *